(12) United States Patent
Knobloch (10) Patent No.: US 11,832,545 B2
(45) Date of Patent: Dec. 5, 2023

(54) SYSTEM AND METHOD FOR OPERATING GROUND ENGAGING TOOLS BASED ON MEASURED SOIL MOISTURE

(71) Applicant: CNH Industrial America LLC, New Holland, PA (US)

(72) Inventor: Dean A. Knobloch, Tuscon, AZ (US)

(73) Assignee: CNH INDUSTRIAL AMERICA LLC, New Holland, PA (US)

( * ) Notice: Subject to any disclaimer, the term of this patent is extended or adjusted under 35 U.S.C. 154(b) by 405 days.

(21) Appl. No.: 16/731,650

(22) Filed: Dec. 31, 2019

(65) Prior Publication Data
US 2021/0195821 A1   Jul. 1, 2021

(51) Int. Cl.
| | |
|---|---|
| A01B 63/28 | (2006.01) |
| G01N 33/24 | (2006.01) |
| A01B 79/00 | (2006.01) |
| A01B 5/04 | (2006.01) |
| A01B 63/00 | (2006.01) |
| A01B 63/10 | (2006.01) |

(52) U.S. Cl.
CPC ............ *A01B 63/28* (2013.01); *G01N 33/246* (2013.01); *A01B 5/04* (2013.01); *A01B 63/008* (2013.01); *A01B 63/10* (2013.01); *A01B 79/005* (2013.01); *G01N 2033/245* (2013.01)

(58) Field of Classification Search
CPC ....... A01B 63/28; A01B 63/008; A01B 63/10; A01B 5/04; A01B 79/005; G01N 33/246; G01N 2033/245
See application file for complete search history.

(56) References Cited

U.S. PATENT DOCUMENTS

| | | |
|---|---|---|
| 5,524,560 A | 6/1996 | Carter |
| 8,430,179 B2 | 4/2013 | Van Buskirk et al. |
| 8,448,717 B2 | 5/2013 | Adams et al. |
| 8,522,889 B2 | 9/2013 | Adams et al. |

(Continued)

FOREIGN PATENT DOCUMENTS

CN         208191167 U       12/2018

OTHER PUBLICATIONS

"Case IH Adds an Innovative Soil Sensor for Controlling Tillage Equipment," Feb. 19, 2018 (3 pages) https://www.caseih.com/emea/en-za/News/Pages/2018-02-19-Case-IH-adds-an-innovative-soil-sensor-for-controlling-tillage-equipment-and-seed-drills-to-its-product-portfoli.aspx.

*Primary Examiner* — Tara Mayo
(74) *Attorney, Agent, or Firm* — Rebecca Henkel; Rickard DeMille (57) ABSTRACT

A system for limiting plugging within an agricultural implement. The system includes a ground engaging tool configured to be supported by the agricultural implement. An actuator is coupled to the ground engaging tool. The actuator is operable to apply a down pressure on the ground engaging tool. A soil moisture sensor is positioned forward of the ground engaging tool. The soil moisture sensor is configured to measure a soil moisture forward of the ground engaging tool. A controller is communicatively coupled to the soil moisture sensor. The controller is configured to receive, from the soil moisture sensor, a signal that corresponds to the soil moisture forward of the ground engaging tool. The controller is further configured to adjust the down pressure on the ground engaging tool applied by the actuator based at least in part on the signal from the soil moisture sensor.

17 Claims, 5 Drawing Sheets

(56) References Cited

U.S. PATENT DOCUMENTS

| | | |
|---|---|---|
| 8,827,001 B2 | 9/2014 | Wendte et al. |
| 8,857,530 B2 | 10/2014 | Henry |
| 9,113,589 B2 | 8/2015 | Bassett |
| 9,554,098 B2 | 1/2017 | Casper et al. |
| 9,629,304 B2 | 4/2017 | Zielke |
| 9,675,004 B2 | 6/2017 | Landphair et al. |
| 9,775,278 B2 | 10/2017 | Zemenchik et al. |
| 10,165,725 B2 | 1/2019 | Sugumaran et al. |
| 2003/0016029 A1 | 1/2003 | Schuler et al. |
| 2011/0102798 A1* | 5/2011 | Holland ............... A01B 79/005 356/445 |
| 2015/0264857 A1* | 9/2015 | Achen et al. .......... A01B 49/06 111/149 |
| 2018/0049361 A1 | 2/2018 | Zemenchik |
| 2018/0070525 A1 | 3/2018 | Adams et al. |
| 2018/0168094 A1* | 6/2018 | Koch et al. ............ A01C 7/203 |
| 2018/0239044 A1 | 8/2018 | Rhodes et al. |
| 2019/0216005 A1* | 7/2019 | Bassett ............... A01B 79/005 |
| 2020/0084954 A1* | 3/2020 | Sporrer et al. ......... A01B 63/32 |
| 2020/0128723 A1* | 4/2020 | Eichhorn ............... G01N 33/24 |
| 2020/0344944 A1* | 11/2020 | Wonderlich et al. .. A01C 7/105 |

\* cited by examiner

SYSTEM AND METHOD FOR OPERATING GROUND ENGAGING TOOLS BASED ON MEASURED SOIL MOISTURE

FIELD OF THE INVENTION

The present disclosure generally relates to agricultural implements and, more particularly, to systems and methods for limiting plugging of ground engaging tools of an agricultural implement, such as rolling basket assemblies, based on measured soil moisture forward of the ground engaging tools.

BACKGROUND OF THE INVENTION

It is well known that, to attain the best agricultural performance from a field, a farmer must cultivate the soil, typically through a tillage operation. Modern farmers perform tillage operations by pulling a tillage implement behind an agricultural work vehicle, such as a tractor. Tillage implements typically include one or more ground engaging tools configured to engage the soil as the implement is moved across the field. For example, in certain configurations, the implement may include one or more harrow discs, leveling discs, rolling baskets, shanks, tines, and/or the like. Such ground engaging tool(s) loosen and/or otherwise agitate the soil to prepare the field for subsequent planting operations.

During tillage operations, field materials, such as residue, soil, rocks, mud, and/or the like, may become trapped or otherwise accumulate on and/or within ground engaging tools or between adjacent ground engaging tools. For instance, material accumulation will often occur around the exterior of a basket assembly (e.g., on the blades or bars of the basket assembly) and/or within the interior of the basket assembly. Such accumulation of field materials may prevent the basket assembly from performing in a desired manner during the performance of a tillage operation. In such instances, it is often necessary for the operator to take certain corrective actions to remove the material accumulation. However, it is typically difficult for the operator to detect or determine a plugged condition of a basket assembly or any other suitable ground engaging tool(s) when viewing the tools from the operator's cab.

Accordingly, an improved system and method for limiting or avoiding plugging of ground engaging tools of an agricultural implement would be welcomed in the technology. A system and method for limiting or avoiding plugging of ground engaging tools of an autonomous agricultural implement would also be useful.

SUMMARY OF THE INVENTION

Aspects and advantages of the technology will be set forth in part in the following description, or may be obvious from the description, or may be learned through practice of the technology.

In one example aspect, the present subject matter is directed to a system for limiting plugging within an agricultural implement. The system includes a ground engaging tool configured to be supported by the agricultural implement. An actuator is coupled to the ground engaging tool. The actuator is operable to apply a down pressure on the ground engaging tool. A soil moisture sensor is positioned forward of the ground engaging tool. The soil moisture sensor is configured to measure a soil moisture forward of the ground engaging tool. A controller is communicatively coupled to the soil moisture sensor. The controller is configured to receive, from the soil moisture sensor, a signal that corresponds to the soil moisture forward of the ground engaging tool. The controller is further configured to adjust the down pressure on the ground engaging tool applied by the actuator based at least in part on the signal from the soil moisture sensor.

In another example aspect, the present subject matter is directed to an agricultural implement. The agricultural implement includes a frame. A basket assembly is configured to be supported by the frame. An actuator is coupled to the basket assembly. The actuator is operable to apply a down pressure on the basket assembly. A soil moisture sensor is positioned forward of the basket assembly. The soil moisture sensor is configured to measure a soil moisture forward of the basket assembly. A controller is communicatively coupled to the soil moisture sensor. The controller is configured to receive, from the soil moisture sensor, a signal that corresponds to the soil moisture forward of the basket assembly. The controller is further configured to adjust the down pressure on the basket assembly applied by the actuator based at least in part on the signal from the soil moisture sensor.

In a further example aspect, the present subject matter is directed to a method for limiting plugging within an agricultural implement. The method includes receiving a signal from a soil moisture sensor positioned forward of a ground engaging tool along a direction of travel of the agricultural implement. The signal corresponds to a measured soil moisture forward of the ground engaging tool. The method also includes comparing, with a computing device, the measured soil moisture forward of the ground engaging tool to a predetermined threshold, and adjusting, with the computing device, a down pressure applied by an actuator on the ground engaging tool in response to the measured soil moisture forward of the ground engaging tool exceeding the predetermined threshold.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for limiting or avoiding plugging of ground engaging tools of an agricultural implement. Specifically, in several embodiments, the disclosed system may include a soil moisture sensor that is operable to measure soil moisture forward of a ground engaging tool. In general, the soil moisture sensor may output a signal that corresponds to the magnitude of soil moisture forward of the ground engaging tool along a direction of travel of the ground engaging tool. When operating in relatively damp or wet soil, field materials accumulate more quickly on, within, and/or adjacent to the ground engaging tool. Conversely, field materials accumulate more slowly (or not at all) on, within, and/or adjacent to the ground engaging tool when operating in relatively dry soil. The measured soil moisture from the soil moisture sensor may be used to determine when the ground engaging tool(s) is/are operating in wet or dry conditions. By monitoring the measured soil moisture from the soil moisture sensor, an associated controller or computing device of the system may infer or determine that the ground engaging tool(s) is/are more likely to become plugged or experience a plugged condition. Once it is determined that the ground engaging tool(s) is/are likely to become plugged, an appropriate control action may then be executed, such as by notifying the operator of the plugged condition or by performing an automated control action. For instance, the associated controller or a user may adjust a down pressure on applied by an actuator on the ground engaging tool. In particular, the associated controller or the user may lift the ground engaging tool with the actuator to avoid plugging the ground engaging tool.

Figure 1:
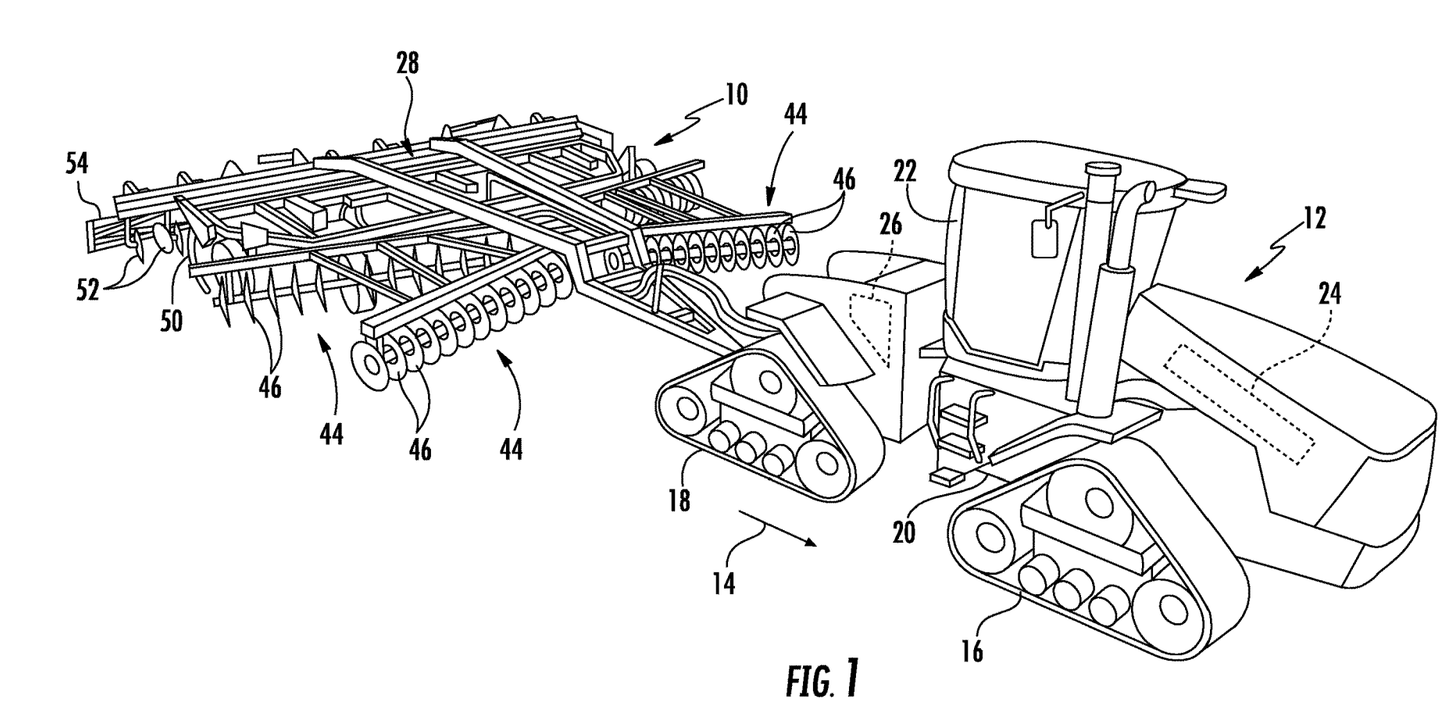
FIG. 1 illustrates a perspective view of one example embodiment of an agricultural implement coupled to a work vehicle in accordance with aspects of the present subject matter.
Figure 2:
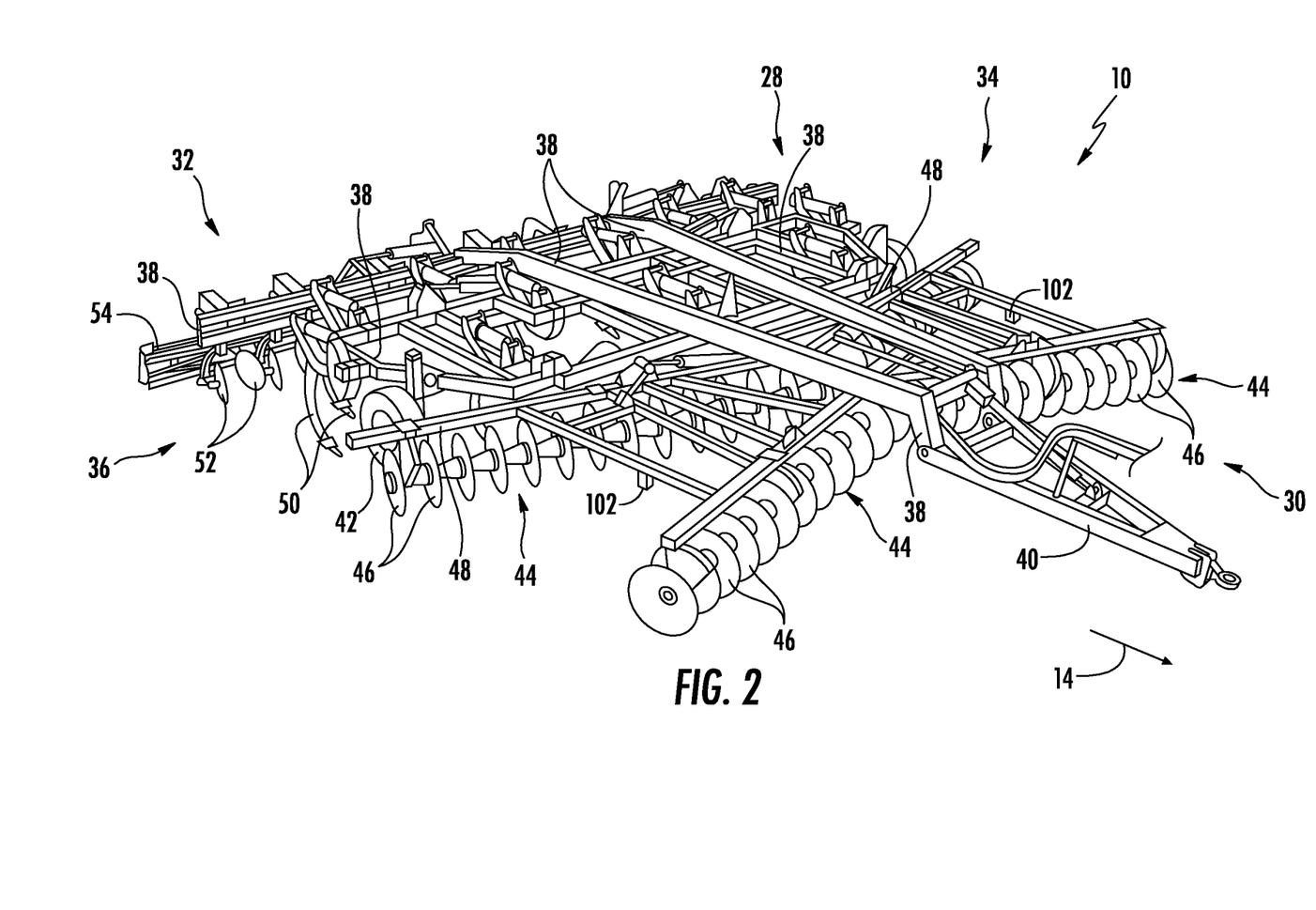
FIG. 2 illustrates another perspective view of the agricultural implement shown in FIG. 1 in accordance with example aspects of the present subject matter.

Referring now to the drawings, FIGS. 1 and 2 illustrate differing perspective views of one embodiment of an agricultural implement 10 in accordance with aspects of the present subject matter. Specifically, FIG. 1 illustrates a perspective view of the agricultural implement 10 coupled to a work vehicle 12. Additionally, FIG. 2 illustrates a perspective view of the implement 10, particularly illustrating various components of the implement 10.

In general, the implement 10 may be configured to be towed across a field in a direction of travel (e.g., as indicated by arrow 14 in FIG. 1) by the work vehicle 12. As shown, the implement 10 may be configured as a tillage implement, and the work vehicle 12 may be configured as an agricultural tractor. However, in other embodiments, the implement 10 may be configured as any other suitable type of implement, such as a seed-planting implement, a fertilizer-dispensing implement, and/or the like. Similarly, the work vehicle 12 may be configured as any other suitable type of vehicle, such as an agricultural harvester, a self-propelled sprayer, and/or the like.

As shown in FIG. 1, the work vehicle 12 may include a pair of front track assemblies 16, a pair or rear track assemblies 18, and a frame or chassis 20 coupled to and supported by the track assemblies 16, 18. An operator's cab 22 may be supported by a portion of the chassis 20 and may house various input devices for permitting an operator to control the operation of one or more components of the work vehicle 12 and/or one or more components of the implement 10. Additionally, as is generally understood, the work vehicle 12 may include an engine 24 and a transmission 26 mounted on the chassis 20. The transmission 26 may be operably coupled to the engine 24 and may provide variably adjusted gear ratios for transferring engine power to the track assemblies 16, 18 via a drive axle assembly (not shown) (or via axles if multiple drive axles are employed).

As shown in FIGS. 1 and 2, the implement 10 may include a frame 28. More specifically, as shown in FIG. 2, the frame 28 may extend longitudinally between a forward end 30 and an aft end 32. The frame 28 may also extend laterally between a first side 34 and a second side 36. In this respect, the frame 28 generally includes a plurality of structural frame members 38, such as beams, bars, and/or the like, configured to support or couple to a plurality of components. Furthermore, a hitch assembly 40 may be connected to the frame 28 and configured to couple the implement 10 to the work vehicle 12. Additionally, a plurality of wheels 42 (one is shown) may be coupled to the frame 28 to facilitate towing the implement 10 in the direction of travel 14.

In several embodiments, the frame 28 may be configured to support various ground engaging tools. For instance, the frame 28 may support one or more gangs or sets 44 of disc blades 46. Each disc blade 46 may be configured to penetrate into or otherwise engage the soil as the implement 10 is being pulled through the field. In this regard, the various disc gangs 44 may be oriented at an angle relative to the direction of travel 14 to promote more effective tilling of the soil. In the embodiment shown in FIGS. 1 and 2, the implement 10 includes four disc gangs 44 supported on the frame 28 adjacent to its forward end 30. However, it should be appreciated that, in alternative embodiments, the implement 10 may include any other suitable number of disc gangs 44, such as more or fewer than four disc gangs 44. Furthermore, in one embodiment, the disc gangs 44 may be mounted to the frame 28 at any other suitable location, such as adjacent to its aft end 32.

Additionally, as shown, in one embodiment, the implement frame 28 may be configured to support other ground engaging tools. For instance, in the illustrated embodiment, the frame 28 is configured to support a plurality of shanks 50 configured to rip or otherwise till the soil as the implement 10 is towed across the field. Furthermore, in the illustrated embodiment, the frame 28 is also configured to support one or more finishing tools, such as a plurality of leveling blades 52 and/or rolling (or crumbler) basket assemblies 54. However, in other embodiments, any other suitable ground-engaging tools may be coupled to and supported by the implement frame 28, such as a plurality closing discs.

Figure 3:
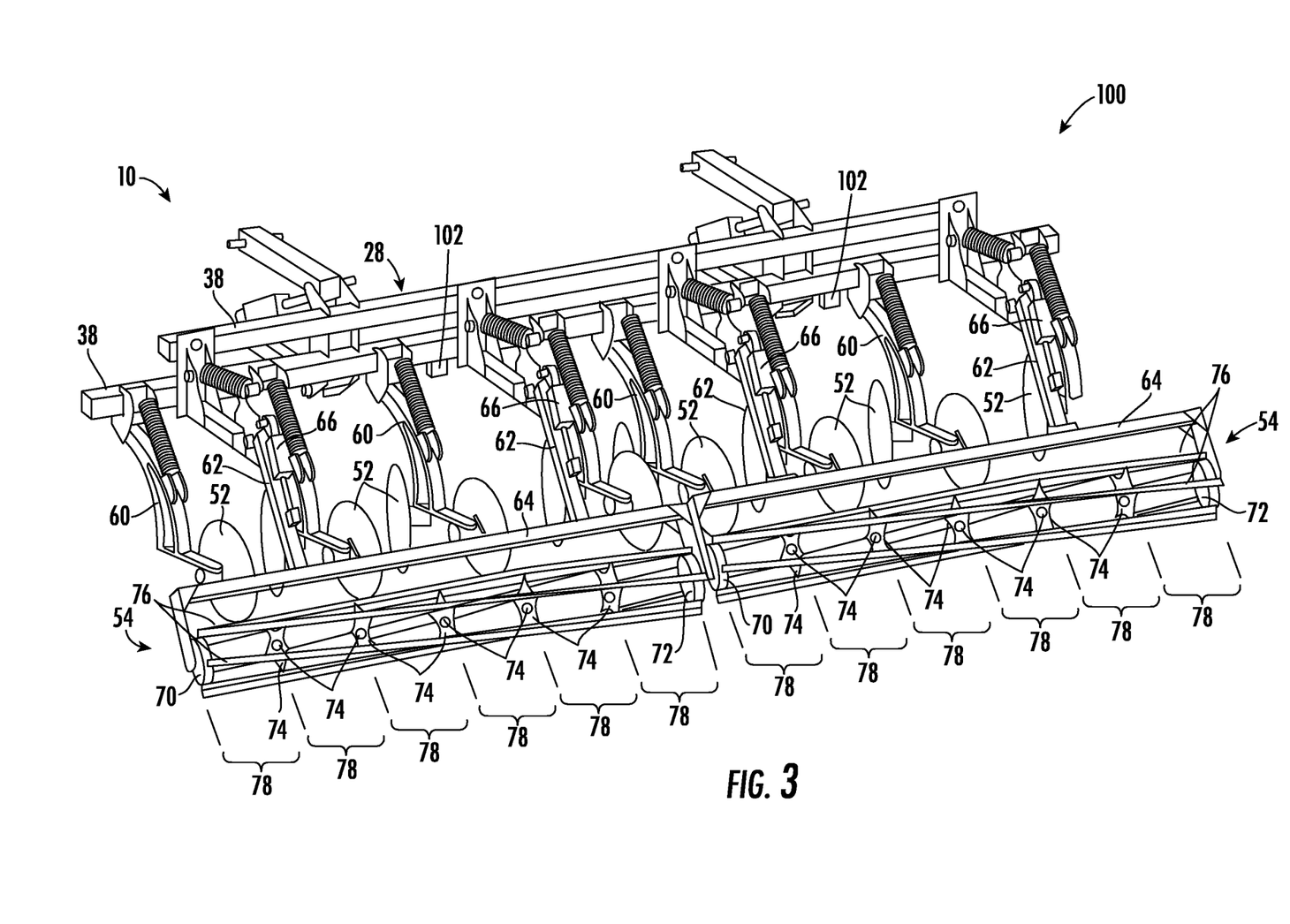
FIG. 3 illustrates a partial perspective view of finishing tools positioned at an aft end of the implement shown in FIGS. 1 and 2, particularly illustrating one embodiment of a system for limiting or avoiding plugging of ground engaging tools provided in operative association with the implement in accordance with aspects of the present subject matter.

Referring now to FIG. 3, a partial, perspective view of the aft end of the implement 10 shown in FIGS. 1 and 2 is illustrated in accordance with aspects of the present subject matter, particularly illustrating a portion of the finishing tools 52, 54 of the implement 10. As shown, the various finishing tools 52, 54 may be coupled to or supported by the implement frame 28, such as by coupling each tool to a toolbar or laterally extending frame member 38 of the frame 38. For instance, as shown in FIG. 3, a blade support arm 60 may be coupled between a given frame member 38 and each leveling blade 52 or set of leveling blades 52 to support the blades 52 relative to the frame 28. Similarly, one or more basket support arms 62 may be coupled between a given frame member 38 and an associated mounting yoke or basket hanger 64 for supporting each basket assembly 54 relative to the frame 28. Additionally, as shown in FIG. 3, in one embodiment, a basket actuator 66 (e.g., a hydraulic or pneumatic cylinder) may be coupled to each basket support arm 62 to allow the down force or down pressure applied to each basket assembly 54 to be adjusted. The basket actuators 66 may also allow the basket assemblies 54 to be raised off the ground, such as when the implement 10 is making a headland turn and/or when the implement 10 is being operated within its transport mode.

In several embodiments, each basket assembly 54 includes a plurality of support plates 70, 72, 74 configured to support a plurality of blades or bars 76 spaced circumferentially about the outer perimeter of the basket. For instance, as shown in FIG. 3, each basket assembly 54 includes first and second end plates 70, 72 positioned at the opposed lateral ends of the basket assembly 54 and a plurality of inner support plates 74 spaced apart laterally from one another between the end plates 70, 72. Lateral basket sections 78 are generally defined between each pair of adjacent support plates 70, 72, 74, with each basket section 78 being generally characterized by a hollow or substantially hollow interior area surrounded by the lateral portions of the bars 76 extending between the respective pair of adjacent support plates 70, 72, 74. As is generally understood, the end plates 70, 72 may be rotatably coupled to the corresponding basket hanger 64 (which, in turn, is coupled to the associated bracket support arm(s) 62) via bearings to allow the basket assembly 54 to rotate relative to the hanger/arm 64, 62 as implement 10 is being moved across the field. Additionally, in the illustrated embodiment, the bars 76 of each basket assembly 54 are configured as formed bars. However, in other embodiments, the bars 76 may have any other suitable configuration, such as flat bars, round bars, and/or the like.

Moreover, in accordance with aspects of the present subject matter, FIG. 3 also illustrates components of one embodiment of a system 100 for limiting or avoiding plugging of ground engaging tools of an agricultural implement. Specifically, in the illustrated embodiment, the system 100 is shown as being configured for use in limiting or avoiding a plugged condition(s) of the basket assemblies 54. However, in other embodiments, the system 100 may be utilized to limit or avoid a plugged condition of any other suitable ground engaging tool(s), such as blades, disks, shanks, and/or the like.

As shown in FIG. 3, the system 100 includes one or more soil moisture sensors 102 configured to measure the moisture in soil over which basket actuators 66 pass. In general, soil moisture sensors 102 may output a signal that corresponds to the soil moisture of soil forward of one or more of basket assemblies 54, e.g., towards forward end 30 (FIG. 2) from basket actuators 66, along a direction of travel of implement 10. Relatively dry field materials accumulate more slowly (or not at all) on, within, and/or adjacent to basket assemblies 54, and relatively damp or wet field materials accumulate more quickly on, within, and/or adjacent to basket assemblies 54. By detecting an increase in the measured soil moisture from soil moisture sensors 102, an associated controller or computing device 106 (FIGS. 4 and 5) of the system 100 may infer or determine that the basket assembly 54 is operating in conditions likely to lead to plugging or a plugged condition. For instance, in one embodiment, the controller 106 may be configured to compare the measured soil moisture from soil moisture sensors 102 to a reference soil moisture, which may correspond to the soil moisture level for dry or non-wet soil in which plugging is unlikely. Once it is determined that the basket assembly 54 is operating in damp or wet soil, an appropriate control action may then be executed, such as by notifying the operator of the damp or wet soil condition or by performing an automated control action.

In several embodiments, one or more of soil moisture sensors 102 may be mounted on toolbar(s) 38 of implement frame 28, basket support arm 62, etc. In alternative example embodiments, soil moisture sensors 102 may be positioned on work vehicle 12 or another suitable portion of implement 10. Soil moisture sensors 102 may be positioned forward of basket assemblies 54 along a direction of travel of implement 10. Thus, e.g., soil moisture sensors 102 may be positioned closer to forward end 30 of frame 28 than basket assemblies 54, e.g., when soil moisture sensors 102 are positioned on implement 10. In such a manner, soil moisture sensors 102 may measure the moisture of soil prior to basket assemblies 54 engaging such soil. In certain example embodiments, soil moisture sensors 102 may be positioned on implement frame 28 such that soil moisture sensors 102 measure the moisture of soil prior to any tillage operation of implement 10. In other example embodiments, soil moisture sensors 102 may be positioned on implement frame 28 such that soil moisture sensors 102 measure the moisture of soil after one or more of the tillage operations of implement 10, e.g., but prior to basket assemblies 54. Soil moisture sensors 102 may be a suitable device for measuring soil moisture. For example, soil moisture sensors 102 may include electrical conductivity sensors, ground penetrating radar sensors, gamma-ray spectrometry sensors, electro-magnetic induction sensors, near-infrared reflectance sensors, etc.

Figure 4:
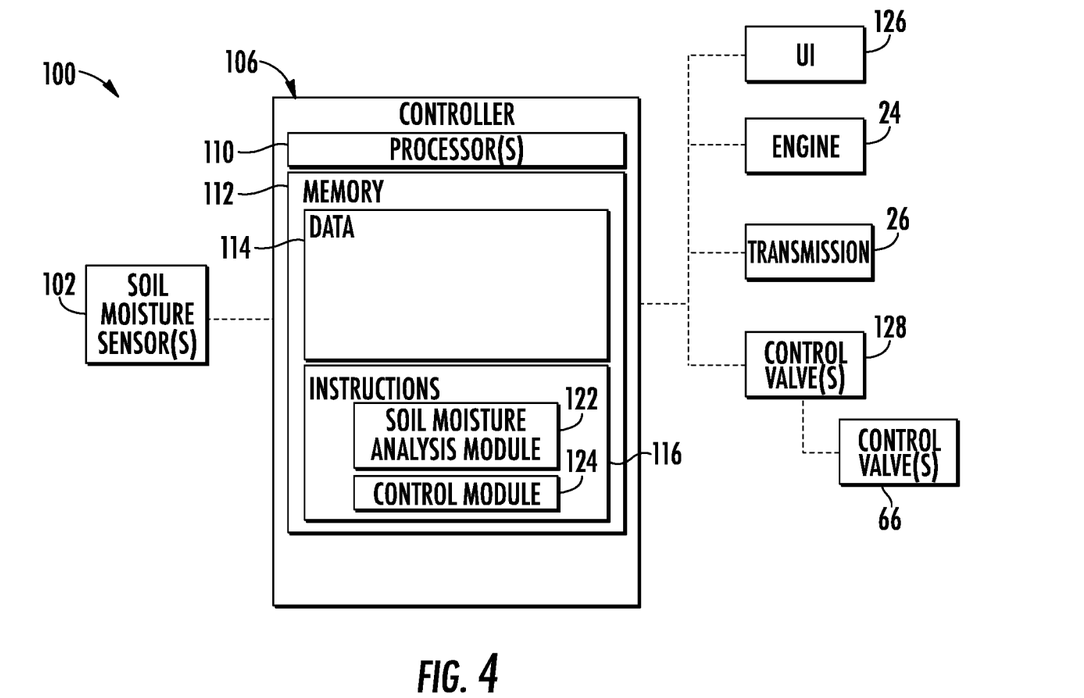
FIG. 4 illustrates a schematic view of one embodiment of a system for limiting or avoiding plugging of ground engaging tools of an agricultural implement in accordance with aspects of the present subject matter.

Referring now to FIG. 4, a schematic view of one embodiment of a system 100 for limiting or avoiding plugging of ground engaging tools of an agricultural implement is illustrated in accordance with aspects of the present subject matter. In general, the system 100 will be described with reference to the implement shown in FIGS. 1 and 2 and the basket assembly 54 and associated system components shown in FIGS. 3 and 4. However, in other embodiments, the disclosed system 100 may be utilized to limit or avoid tool plugging in association with any other suitable agricultural implement having any other suitable implement configuration and/or with any other suitable ground engaging tool(s) having any other suitable tool configuration.

As indicated above, in several embodiments, the system 100 may include one or more soil moisture sensors 102 operable to measure soil moisture forward of a ground engaging tool (e.g., basket assembly 54). Additionally, as indicated above, the system 100 may also include a controller 106 communicatively coupled to the soil moisture sensor(s) 102. As will be described in greater detail below, controller 106 may be configured to analyze the signals received from soil moisture sensors 102 and/or related data 114 associated with such signals to infer the existence of material accumulation on, within, and/or adjacent to the associated ground engaging tool. Additionally, the controller 106 may also be configured to execute one or more control actions in response to the determination that the associated ground engaging tool is likely to plug or in the process of becoming plugged. For instance, in one embodiment, the controller 106 may notify the operator that the tool is likely to become plugged in the near future. In addition to notifying the operator (or as an alternative thereto), the controller 106 may be configured to execute one or more automated control actions adapted to avoid or limit plugging of the ground engaging tool or otherwise reduce the amount of material accumulation on, within, and/or adjacent to the ground engaging tool, such as by automatically adjusting the speed of the implement 10 and/or the down force applied to the ground engaging tool and/or by automatically raising and lowering the ground engaging tool relative to the ground. As a particular example, the controller 106 may adjust a down pressure on the ground engaging tool applied by an actuator coupled to the ground engaging tool based at least in part on the signal from the soil moisture sensor 102. For instance, the controller 106 may adjust the down pressure on the ground engaging tool applied by the actuator as a function of the measured soil moisture from the soil moisture sensor 102. Thus, e.g., as the measured soil moisture from the soil moisture sensor 102 increases, the controller 106 may decrease the down pressure on the ground engaging tool applied by the actuator. In addition or alternatively, controller 106 may operate the actuator to lift the ground engaging tool away from the damp or wet soil as the measured soil moisture from the soil moisture sensor 102 increases.

In general, the controller 106 may correspond to any suitable processor-based device(s), such as a computing device or any combination of computing devices. Thus, as shown in FIG. 4, the controller 106 may generally include one or more processor(s) 110 and associated memory devices 112 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 112 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 112 may generally be configured to store suitable computer-readable instructions that, when implemented by the processor(s) 110, configure the controller 106 to perform various computer-implemented functions, such as one or more aspects of the method 200 described below with reference to FIG. 4. In addition, controller 106 may also include various other suitable components, such as a communications circuit or module, one or more input/output channels, a data/control bus and/or the like.

It should be appreciated that controller 106 may correspond to an existing controller of the implement 10 or the work vehicle 12 or controller 106 may correspond to a separate processing device. For instance, in one embodiment, controller 106 may form all or part of a separate plug-in module that may be installed within the implement 10 or the work vehicle 12 to allow for the disclosed system and method to be implemented without requiring additional software to be uploaded onto existing control devices of the implement 10 or the work vehicle 12.

Referring still to FIG. 3, in several embodiments, the instructions 116 stored within the memory 112 of the controller 102 may be executed by the processor(s) 110 to implement a soil moisture monitoring module 122. In general, the soil moisture monitoring module 122 may be configured to analyze the signals received from soil moisture sensor(s) 102 and/or the related signal data to estimate or infer when the associated ground engaging tool is likely to plug. Specifically, in several embodiments, the soil moisture monitoring module 122 may be configured to compare a current operating soil moisture forward of the ground engaging tool to an associated soil moisture threshold. For instance, in one embodiment, a soil moisture threshold calibration may be stored within memory 112. The soil moisture threshold calibration may be received from soil moisture sensor(s) 102 when the associated ground engaging tool is known to over suitably dry soil. Thus, the soil moisture threshold calibration may correspond to the soil moisture corresponding to a reduced likelihood of plugging such that the ground engaging tool may freely operate in an unplugged state when the soil moisture measured by the soil moisture sensor(s) 102 is less than the soil moisture threshold calibration. In several alternative embodiments, the associated soil moisture threshold may be selected by a manufacturer of system 100 and/or correspond to an estimate for the soil moisture of dry or non-wet soil. When the current operating soil moisture from soil moisture sensor(s) 102 exceeds the soil moisture threshold calibration by a predetermined amount, the controller 106 may then infer or estimate that the ground engaging tool is likely to plug and may initiate appropriate control actions in response to such condition.

In certain example embodiments, soil moisture sensors 102 may also be operable to detect a soil type forward of the ground engaging tool (e.g., basket assembly 54). The soil type may affect the acceptable soil moisture level for limiting or avoiding plugging the ground engaging tool. Thus, the controller 106 may utilize a respective soil moisture threshold calibration for each soil type identified by soil moisture sensors 102.

Referring still to FIG. 3, the instructions 116 stored within the memory 112 of the controller 102 may also be executed by the processor(s) 110 to implement a control module 124. In general, the control module 124 may be configured to initiate a control action when it is determined that a ground engaging tool of the implement 10 is plugged. As indicated above, in one embodiment, the control module 124 may be configured to provide a notification to the operator of the vehicle/implement 12/10 indicating that material accumulation is likely on, within, and/or adjacent to one or more of the ground engaging tools of the implement 10. For instance, in one embodiment, the control module 124 may causing a visual or audible notification or indicator to be presented to the operator via an associated user interface 126 provided within the cab 22 of the vehicle 10.

In other embodiments, the control module 124 may be configured to execute an automated control action designed to adjust the operation of the implement 10. For instance, in one embodiment, the controller 102 may be configured to increase or decrease the operational or ground speed of the implement 10 in an attempt to reduce the amount of material accumulation and/or to limit further material accumulation.

For instance, as shown in FIG. 4, the controller 106 may be communicatively coupled to both the engine 24 and the transmission 26 of the work vehicle 12. In such an embodiment, the controller 106 may be configured to adjust the operation of the engine 24 and/or the transmission 26 in a manner that increases or decreases the ground speed of the work vehicle 12 and, thus, the ground speed of the implement 10, such as by transmitting suitable control signals for controlling an engine or speed governor (not shown) associated with the engine 24 and/or transmitting suitable control signals for controlling the engagement/disengagement of one or more clutches (not shown) provided in operative association with the transmission 26. It should be appreciated that controller 106 may also be configured to decrease the ground speed in a manner that brings vehicle/implement 12/10 to a complete stop.

In addition to the adjusting the ground speed of the vehicle/implement 12, 10 (or as an alternative thereto), the controller 102 may also be configured to adjust an operating parameter associated with the ground-engaging tools of the implement 10. For instance, as shown in FIG. 4, the controller 102 may be communicatively coupled to one or more valves 128 configured to regulate the supply of fluid (e.g., hydraulic fluid or air) to one or more corresponding actuators of the implement 10. In such an embodiment, by regulating the supply of fluid to the actuator(s), the controller 106 may automatically adjust the penetration depth, the down pressure, and/or any other suitable operating parameter associated with the ground-engaging tools of the implement 10. For instance, by controlling the operation of the basket actuators 66, the controller 106 may automatically adjust the down pressure applied to the associated basket assembly 54. Additionally, the controller 106 may control the operation of the basket actuator 66 to raise and lower the associated basket assembly 54 relative to the ground. In such a manner, the amount of material accumulation on basket assembly 54 may be advantageously reduced, e.g., the basket assembly 54 may avoid plugging.

Figure 5:
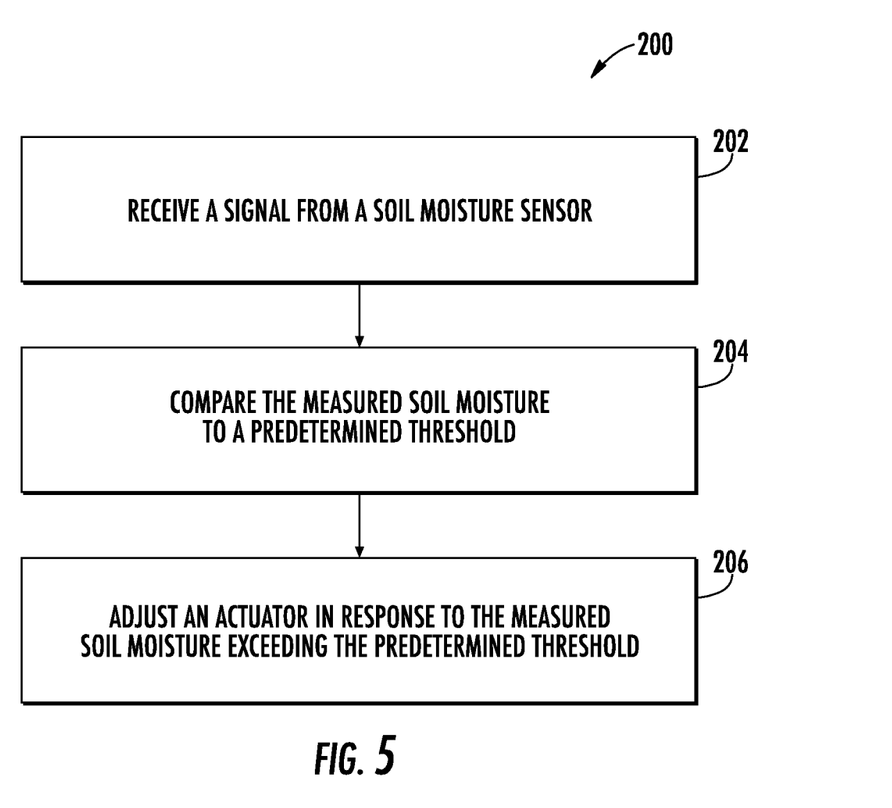
FIG. 5 illustrates a flow diagram of one embodiment of a method for limiting or avoiding plugging of ground engaging tools of an agricultural implement in accordance with aspects of the present subject matter.

Referring now to FIG. 5, a flow diagram of one embodiment of a method 200 for limiting or avoiding plugging of ground engaging tools of an agricultural implement is illustrated in accordance with aspects of the present subject matter. In general, the method 200 will be described herein with reference to the agricultural implement 10, the basket assembly 54, and the system 100 described above with reference to FIGS. 1 through 5. However, it should be appreciated by those of ordinary skill in the art that the disclosed method 200 may generally be implemented with any agricultural implement having any suitable implement configuration, any ground engaging tool having any suitable tool configuration, and/or any system having any suitable system configuration. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (202), the method 200 may include receiving a signal from a soil moisture sensor, e.g., while an actuator for a ground engaging tool of an agricultural implement positions the ground engaging tool in contact with the ground. In particular, the basket assemblies 54 may be lowered to the ground by basket actuators 66 at (202). As described above with reference to FIG. 3, the signals from each soil moisture sensor 102 may be received by the associated system controller 106. The signal(s) from soil moisture sensor(s) 102 correspond to the soil moisture forward of one or more basket assemblies 54. Soil moisture sensor(s) 102 may also detect a soil type at (202).

Additionally, at (204), the method 200 may include comparing, the measured soil moisture from (202) to a predetermined threshold. In particular, the controller 106 may be configured to analyze the signals received from soil moisture sensor(s) 102 and compare the signals to predetermined threshold(s). Specifically, as indicated above, the controller 106 may be configured to compare the signals from soil moisture sensor(s) 102 and/or data related to such signals to determine whether the measured soil moisture from (202) is/are significantly greater than a reference soil moisture, e.g., that corresponds to dry or non-wet soil. The controller 106 may select a particular reference soil moisture based on the soil type detected by soil moisture sensor(s) 102 at (202).

The method 200 may include identifying that the ground engaging tool is likely to plug in response to the determination that the measured soil moisture exceeds the predetermined threshold at (204). For instance, as indicated above, the controller 106 may be configured to infer or estimate that a ground engaging tool is susceptible to plugging when controller 106 determines that the signal from soil moisture sensor 102 exceeds the reference soil moisture by more than a predetermined value and/or that the soil is damp or wet.

Moreover, as shown in FIG. 5, at (206), method 200 may include adjusting the actuator for the ground engaging tool in response to the determination that the measured soil moisture exceeds the predetermined threshold at (204). For instance, as indicated above, the controller 106 may be configured to decrease the down pressure applied to the ground engaging tool by the actuator when controller 106 determines that the signal from soil moisture sensor 102 exceeds the reference soil moisture by more than a predetermined value and/or that the soil is damp or wet. As another example, the controller 106 may be configured to lift the ground engaging tool with the actuator (e.g., such that the ground engaging tool does not contact the measured soil) when controller 106 determines that the signal from soil moisture sensor 102 exceeds the reference soil moisture by more than a predetermined value and/or that the soil is damp or wet.

It is to be understood that the steps of the method 200 are performed by the controller 106 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 106 described herein, such as the method 200, is implemented in software code or instructions which are tangibly stored on a tangible computer readable medium. The controller 106 loads the software code or instructions via a direct interface with the computer readable medium or via a wired and/or wireless network. Upon loading and executing such software code or instructions by the controller 106, the controller 106 may perform any of the functionality of the controller 106 described herein, including any steps of the method 200 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. A system for limiting plugging within an agricultural implement, comprising:
   a ground engaging tool configured to till a field and be supported by the agricultural implement;
   an actuator coupled to the ground engaging tool, the actuator operable to apply a down pressure on the ground engaging tool;
   one or more soil moisture sensors positioned forward of the ground engaging tool, the one or more soil moisture sensors configured to measure a soil moisture forward of the ground engaging tool; and
   a controller communicatively coupled to the one or more soil moisture sensors, the controller configured to:
   receive, from the one or more soil moisture sensors, a first signal that corresponds to the soil moisture forward of the ground engaging tool and a second signal that corresponds to a soil type forward of the ground engaging tool;
   compare the first signal to the second signal; and
   activate the actuator to adjust a down pressure applied by the ground engaging tool in response to the second signal deviating from the first signal by more than a predetermined threshold.

2. The system of claim 1, wherein the controller is configured to decrease the down pressure on the ground engaging tool applied by the actuator in response to the soil moisture forward of the ground engaging tool measured by the one or more soil moisture sensors being greater than the predetermined threshold.

3. The system of claim 2, wherein the controller is configured to increase the down pressure on the ground engaging tool applied by the actuator in response to the soil moisture forward of the ground engaging tool measured by the one or more soil moisture sensors being less than the predetermined threshold.

4. The system of claim 1, wherein the one or more soil moisture sensors is positioned on the agricultural implement forward of the ground engaging tool.

5. The system of claim 1, wherein the one or more soil moisture sensors comprises one or more of an electrical conductivity soil moisture sensor, a ground penetrating radar soil moisture sensor, a gamma-ray spectrometry soil moisture sensor, an electro-magnetic induction soil moisture sensor, and a near-infrared reflectance soil moisture sensor.

6. The system of claim 1, wherein the ground engaging tool comprises one or more of a disk blade, a shank, a leveling blade, and a rolling basket.

7. An agricultural implement, comprising:
   a frame;
   a basket assembly configured to be supported by the frame;
   an actuator coupled to the basket assembly, the actuator operable to alter a position of the basket assembly relative to a frame member;
   a soil moisture sensor positioned forward of the basket assembly, the soil moisture sensor configured to measure a soil moisture forward of the basket assembly; and
   a controller communicatively coupled to the soil moisture sensor, the controller configured to receive, from the soil moisture sensor, a signal that corresponds to the soil moisture forward of the basket assembly, the controller further configured to raise the basket assembly relative to the frame member to a position above a ground surface through activation of the actuator based at least in part on the signal from the soil moisture sensor.

8. The agricultural implement of claim 7, wherein the soil moisture sensor is positioned on the frame forward of the basket assembly.

9. The agricultural implement of claim 7, wherein the soil moisture sensor comprises one or more of an electrical conductivity soil moisture sensor, a ground penetrating radar soil moisture sensor, a gamma-ray spectrometry soil moisture sensor, an electro-magnetic induction soil moisture sensor, and a near-infrared reflectance soil moisture sensor.

10. A method for limiting plugging within an agricultural implement, comprising:
    receiving a first signal from a soil moisture sensor positioned forward of a ground engaging tool configured to till a field along a direction of travel of the agricultural implement, the first signal corresponding to a measured soil moisture forward of the ground engaging tool during a first process;
    receiving a second signal from the soil moisture sensor, the second signal corresponding to a measured soil moisture forward of the ground engaging tool after the first process;
    comparing, with a computing device, the first signal to the second signal; and
    adjusting, with the computing device, a down pressure applied by an actuator on the ground engaging tool in response to the second signal deviating from the first signal by more than a predetermined threshold.

11. The method of claim 10, further comprising controlling an operation of the agricultural implement to adjust an operating parameter associated with the agricultural implement when the ground engaging tool is plugged.

12. The method of claim 10, further comprising notifying an operator of the agricultural implement when the soil moisture forward of the ground engaging tool exceeds the predetermined threshold.

13. The method of claim 10, wherein adjusting the down pressure comprises decreasing the down pressure on the ground engaging tool applied by the actuator in response to the measured soil moisture forward of the ground engaging tool being greater than the predetermined threshold.

14. The method of claim 13, wherein adjusting the down pressure comprises increasing the down pressure on the ground engaging tool applied by the actuator in response to the measured soil moisture forward of the ground engaging tool being less than another predetermined threshold.

15. The method of claim 10, wherein the soil moisture sensor comprises one or more of an electrical conductivity soil moisture sensor, a ground penetrating radar soil moisture sensor, a gamma-ray spectrometry soil moisture sensor, an electro-magnetic induction soil moisture sensor, and a near-infrared reflectance soil moisture sensor.

16. The method of claim 10, wherein the ground engaging tool comprises one or more of a disk blade, a shank, a leveling blade, and a rolling basket.

17. The method of claim 10, wherein the first process is a calibration process.

* * * * *